US010799902B2

(12) United States Patent
Maeda et al.

(10) Patent No.: US 10,799,902 B2
(45) Date of Patent: Oct. 13, 2020

(54) ULTRASONIC NEBULIZER

(71) Applicant: OMRON HEALTHCARE CO., LTD., Muko-shi, Kyoto (JP)

(72) Inventors: Masao Maeda, Kyoto (JP); Takaaki Okanishi, Kyoto (JP); Makoto Tabata, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 533 days.

(21) Appl. No.: 15/697,819

(22) Filed: Sep. 7, 2017

(65) Prior Publication Data

US 2017/0361345 A1 Dec. 21, 2017

Related U.S. Application Data

(63) Continuation of application No. PCT/JP2016/050864, filed on Jan. 13, 2016.

(30) Foreign Application Priority Data

Mar. 25, 2015 (JP) ................................ 2015-063260

(51) Int. Cl.
*B05B 12/08* (2006.01)
*A61M 15/00* (2006.01)
(Continued)

(52) U.S. Cl.
CPC ......... *B05B 12/081* (2013.01); *A61M 11/005* (2013.01); *A61M 15/0085* (2013.01); (Continued)

(58) Field of Classification Search
CPC ............................ A61M 11/00; A61M 11/005; A61M 11/0085; A61M 16/14; A61M 16/16; A61M 16/108; F24F 6/008
See application file for complete search history.

(56) References Cited

U.S. PATENT DOCUMENTS 5,511,539 A * 4/1996 Lien .................. A61M 15/0085
128/200.14
5,881,714 A * 3/1999 Yokoi .................. A61M 11/005
128/200.14
(Continued)

FOREIGN PATENT DOCUMENTS

JP H04-099255 U 8/1992
JP H05-137786 A 6/1993
(Continued)

OTHER PUBLICATIONS

Apr. 5, 2016 International Search Report issued in International Patent Application No. PCT/JP2016/050864.

*Primary Examiner* — Samchuan C Yao
*Assistant Examiner* — Margaret M Luarca
(74) *Attorney, Agent, or Firm* — Oliff PLC

(57) ABSTRACT

An ultrasonic nebulizer includes a tank unit configured to be detachable with respect to a main body. The tank unit includes a working tank in which an ultrasonic vibrator is incorporated, a medicine tank, and a medicine tank cover, which are arranged overlaid in the stated order. The output of an oscillation circuit in the main body is applied to the ultrasonic vibrator through a main body-side contact electrode and a tank-side contact electrode when the tank unit is mounted on the main body. The main body includes an air fan that blows air into the medicine tank through an air duct of the medicine tank cover, and a medicine tank cover detection unit that detects whether or not the air duct of the medicine tank cover is adjacent to the main body so as to detect whether or not the tank unit is mounted on the main body.

4 Claims, 9 Drawing Sheets

(51) Int. Cl.
    *A61M 11/00*     (2006.01)
    *A61M 16/14*     (2006.01)
    *B05B 7/00*       (2006.01)
    *B05B 17/06*      (2006.01)
    *G01F 23/28*      (2006.01)
    *A61M 16/06*      (2006.01)
    *A61M 16/00*      (2006.01)

(52) U.S. Cl.
    CPC ........... *A61M 16/14* (2013.01); *B05B 7/0012* (2013.01); *B05B 17/06* (2013.01); *B05B 17/0615* (2013.01); *G01F 23/28* (2013.01); *A61M 16/0066* (2013.01); *A61M 16/06* (2013.01); *A61M 2205/14* (2013.01); *A61M 2205/276* (2013.01); *A61M 2205/3317* (2013.01); *A61M 2205/3375* (2013.01); *A61M 2205/3382* (2013.01); *A61M 2205/3606* (2013.01); *A61M 2205/502* (2013.01)

(56) References Cited

U.S. PATENT DOCUMENTS

2006/0243274 A1\* 11/2006 Lieberman ........... A61M 11/005
                                                                  128/200.14
2008/0264413 A1\* 10/2008 Doherty ............. A61M 16/021
                                                                  128/202.27
2011/0290241 A1\* 12/2011 Maeda ................ A61M 11/005
                                                                  128/200.14

FOREIGN PATENT DOCUMENTS

| | | |
|---|---|---|
| JP | H05-070668 U | 9/1993 |
| JP | 2002-000730 A | 1/2002 |
| JP | 2004-121605 A | 4/2004 |
| JP | 2005-278742 A | 10/2005 |
| JP | 2006-217955 A | 8/2006 |
| WO | 2010/106834 A1 | 9/2010 |

\* cited by examiner

ULTRASONIC NEBULIZER

TECHNICAL FIELD

This invention relates to an ultrasonic nebulizer. More specifically, this invention relates to an ultrasonic nebulizer that transmits ultrasonic vibration generated by an ultrasonic vibrator to a medicine tank via a working liquid in a working tank and thereby atomizes a medicinal liquid in the medicine tank.

BACKGROUND ART

Conventionally, as disclosed in Patent Document 1 (JP H05-137786A), for example, there is known to be an ultrasonic nebulizer that transmits ultrasonic vibration generated by an ultrasonic vibrator to an atomization tank (medicine tank) via a working liquid in a working tank so as to atomize a medicinal liquid in the atomization tank.

CITATION LIST

Patent Literature

Patent Document 1: JP H05-137786A

SUMMARY OF INVENTION

Technical Problem

Incidentally, the applicant of the present invention has proposed, in another application, this type of ultrasonic nebulizer, which includes a working tank (more specifically, a tank unit including a working tank, a medicine tank, and a medicine tank cover) that is configured to be detachable with respect to a main body. The object thereof is to make it possible for a user (a doctor, a nurse, or the like) to easily clean and/or disinfect the working tank from a hygienic viewpoint, such as preventing the risk of infection.

With this ultrasonic nebulizer, accompanying the tank unit being configured to be detachable with respect to the main body, a main body-side contact electrode is provided on the main body, and a tank-side contact electrode is provided on the tank unit. When the tank unit is mounted on the main body, the output of an oscillation circuit is applied from the main body to the ultrasonic vibrator through the main body-side contact electrode and the tank-side contact electrode. Accordingly, ultrasonic vibration generated by the ultrasonic vibrator is transmitted to the medicine tank via the working liquid in the working tank, and the medicinal liquid in the medicine tank is atomized.

Here, theoretically, if the tank unit is not mounted on the main body, the output of the oscillation circuit appears in the exposed main body-side contact electrode when the atomization operation is started simply based on an operation performed by the user. For this reason, there is a risk that the user will receive an electric shock by touching the main body-side contact electrode. Also, with a format of simply detecting whether or not the multiple elements constituting the above-described tank unit have been mounted, the configuration is more complicated.

In view of this, it is an object of the present invention to provide an ultrasonic nebulizer that includes a tank unit that is configured to be detachable with respect to a main body, and according to which it is possible to eliminate the risk of electric shock with a simple configuration.

Solution to the Problem

In order to solve the foregoing problems, an ultrasonic nebulizer of the present invention includes a tank unit configured to be detachable with respect to a main body, wherein the tank unit includes:
    a working tank in which an ultrasonic vibrator is incorporated and in which a working liquid is contained facing the ultrasonic vibrator;
    a medicine tank that stores a medicinal liquid, at least a bottom portion thereof being dipped in the working liquid; and
    a medicine tank cover that covers an upper portion of the medicine tank and has an air duct that is adjacent to the main body when the tank unit is mounted on the main body, and that takes in blown air from the main body side,
    the working tank, the medicine tank, and the medicine tank cover being arranged by being overlaid in the stated order,
    the tank unit further includes a tank-side contact electrode that is connected to an electrode of the ultrasonic vibrator,
    the main body includes:
    an oscillation circuit that is to drive the ultrasonic vibrator; and
    a main body-side contact electrode that is to emit an output of the oscillation circuit,
    the output of the oscillation circuit being applied to the ultrasonic vibrator through the main body-side contact electrode and the tank-side contact electrode when the tank unit is mounted on the main body, and
    the main body further includes:
    an air fan configured to blow air into the medicine tank through the air duct of the medicine tank cover; and
    a medicine tank cover detection unit configured to detect whether or not the air duct of the medicine tank cover is adjacent to the main body, so as to detect whether or not the tank unit is mounted on the main body.

In the present specification, a tank unit being configured to be "detachable" from the main body means the tank unit has a form in which the tank unit can be mounted on the main body and has a form in which the tank unit can be removed from the main body.

Also, the "working liquid" need only be a medium through which ultrasonic vibration can be transmitted, and water is typically used thereas. Examples of the "medicinal liquid" include a saline solution, or a liquid mixture of a saline solution and Bisolvon.

With the ultrasonic nebulizer of the present invention, the above-described tank unit includes a working tank, a medicine tank, and a medicine tank cover, which are arranged by being overlaid in the stated order. In other words, if the working tank and the medicine tank are not arranged, the medicine tank cover cannot be arranged. Accordingly, if the medicine tank cover detection unit detects that the air duct of the medicine tank cover is adjacent to the main body (i.e., detects that the medicine tank cover has been correctly mounted), it is judged that all of the elements (including the working tank, the medicine tank, and the medicine tank cover) that constitute the tank unit have been mounted on the main body. In this case, since the user is blocked by the tank unit and thus cannot touch the main body-side contact electrode, there is no risk that the user will receive an electric shock, even if the output of the oscillation circuit appears in the main body-side contact electrode. On the other hand, if the medicine tank cover detection unit detects that the air duct of the medicine tank cover is not adjacent to the main body, there is a possibility that at least the medicine tank cover among the elements constituting the tank unit has not been mounted on the main body. If the medicine tank cover has not been mounted, there is a possibility that another constituent element (working tank, medicine tank) of the tank unit has not been mounted on the main body as well. Accordingly, there is a risk that the user will touch the main body-side contact electrode when the output of the oscillation circuit appears in the main body-side contact electrode.

Based on this idea, with the ultrasonic nebulizer of the present invention, the medicine tank cover detection unit detects whether or not the air duct of the medicine tank cover is adjacent to the main body so as to detect whether or not the tank unit has been mounted on the main body. Accordingly, it is possible to eliminate the risk of electric shock even if it is not detected whether or not the working tank included in the tank unit has been mounted. Accordingly, it is possible to eliminate the risk of electric shock with a simple configuration.

Note that with this ultrasonic nebulizer, at the time of the spraying operation, the output of the oscillation circuit is applied to the ultrasonic vibrator through the main body-side contact electrode and the tank-side contact electrode. Accordingly, the ultrasonic vibration generated by the ultrasonic vibrator is transmitted to the medicine tank via the working liquid in the working tank, whereby the medicinal liquid in the medicine tank is atomized. The atomized medicinal liquid is emitted with blown air taken into the medicine tank through the air duct.

An ultrasonic nebulizer of an embodiment includes a control unit configured to perform control for permitting or prohibiting an atomization operation based on an operation start condition, which is that the medicine cover detection unit has detected that the air duct is adjacent to the main body.

With the ultrasonic nebulizer of this embodiment, the control unit performs control for permitting or prohibiting the atomization operation based on an operation start condition, which is that the medicine tank cover detection unit has detected that the air duct is adjacent to the main body.

When the air duct is adjacent to the main body, or in other words, when the tank unit is mounted on the main body, if other operation start conditions are satisfied, the atomization operation is permitted by the control unit. Accordingly, the output of the oscillation circuit can be applied from the main body to the ultrasonic vibrator through the main body-side contact electrode and the tank-side contact electrode. Accordingly, the ultrasonic vibration generated by the ultrasonic vibrator is transmitted to the medicine tank via the working liquid in the working tank, whereby the medicinal liquid in the medicine tank is atomized. The atomized medicinal liquid is emitted with blown air taken into the medicine tank through the air duct.

Note that examples of the "other operation start conditions" include the cooling fan for cooling the oscillation circuit not stopping (locking), and the air cover that covers the air fan being mounted.

On the other hand, when the air duct is not adjacent to the main body, or in other words, when there is a possibility that the working tank and the medicine tank of the tank unit have not been mounted on the main body, the atomization operation is prohibited by the control unit. In other words, the output of the oscillation circuit is prohibited from appearing in the main body-side contact electrode. Accordingly, there is no risk of receiving an electric shock, even if the user touches the main body-side contact electrode.

With an ultrasonic nebulizer of an embodiment, a magnet is incorporated in the air duct, and the medicine tank cover detection unit uses the magnetic force of the magnet to detect whether or not the air duct is adjacent to the main body.

With the ultrasonic nebulizer of the embodiment, a magnet is incorporated in the air duct. The medicine tank cover detection unit uses the magnetic force of the magnet to detect whether or not the air duct is adjacent to the main body. In the case of doing so, the medicine tank cover detection unit can be constituted easily and inexpensively using a hole IC (an integrated circuit including a magnetic sensor), for example.

Advantageous Effects of the Invention

As is evident from the above description, according to the ultrasonic nebulizer of the present invention, it is possible to eliminate the risk of electric shock with a simple configuration.

DESCRIPTION OF EMBODIMENTS

Hereinafter, embodiments of the present invention will be described in detail with reference to the drawings.

Figure 1:
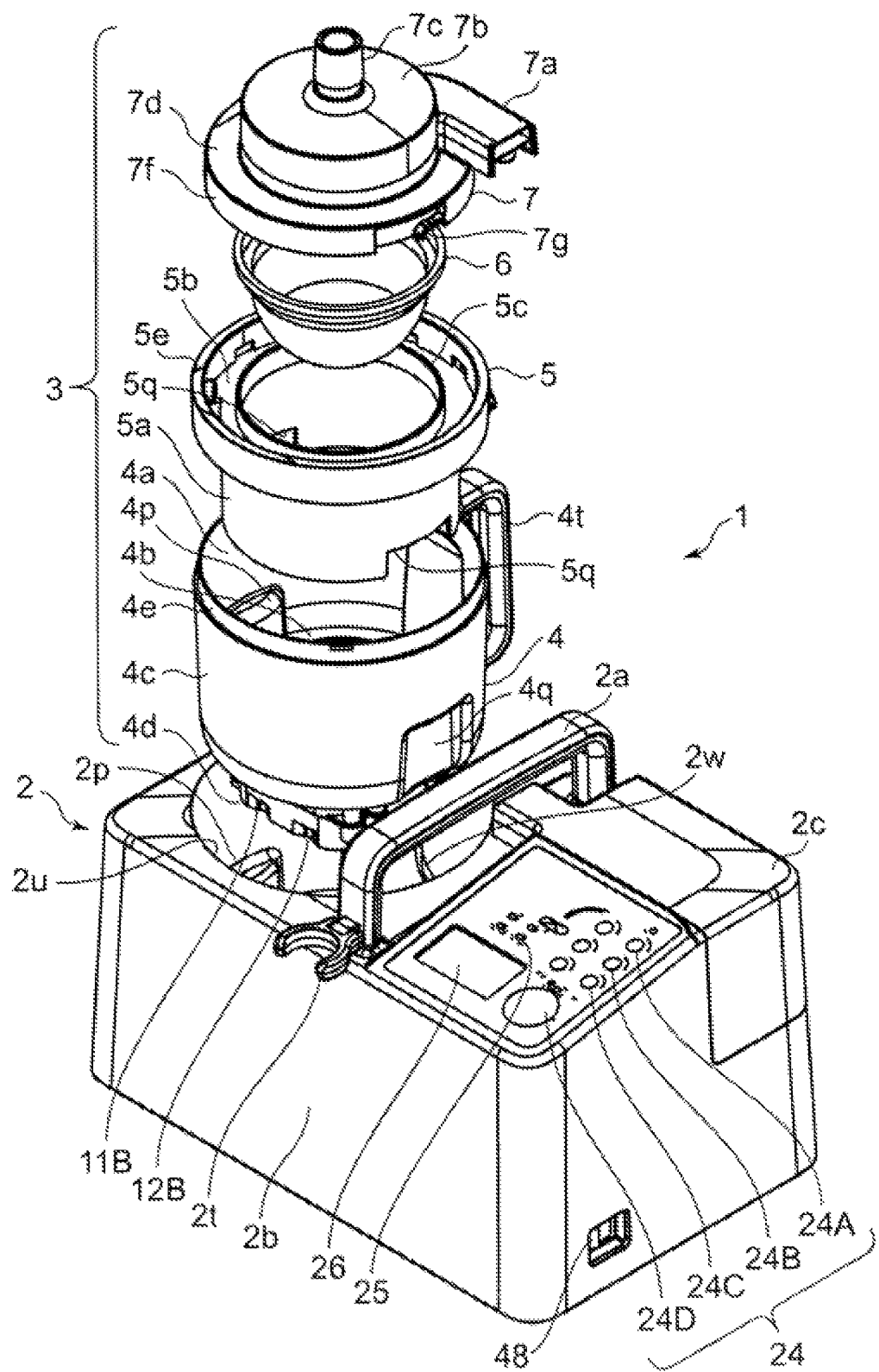
FIG. 1 is a diagram showing an exploded view from above and obliquely to the right of an ultrasonic nebulizer of an embodiment of the invention.
Figure 2:
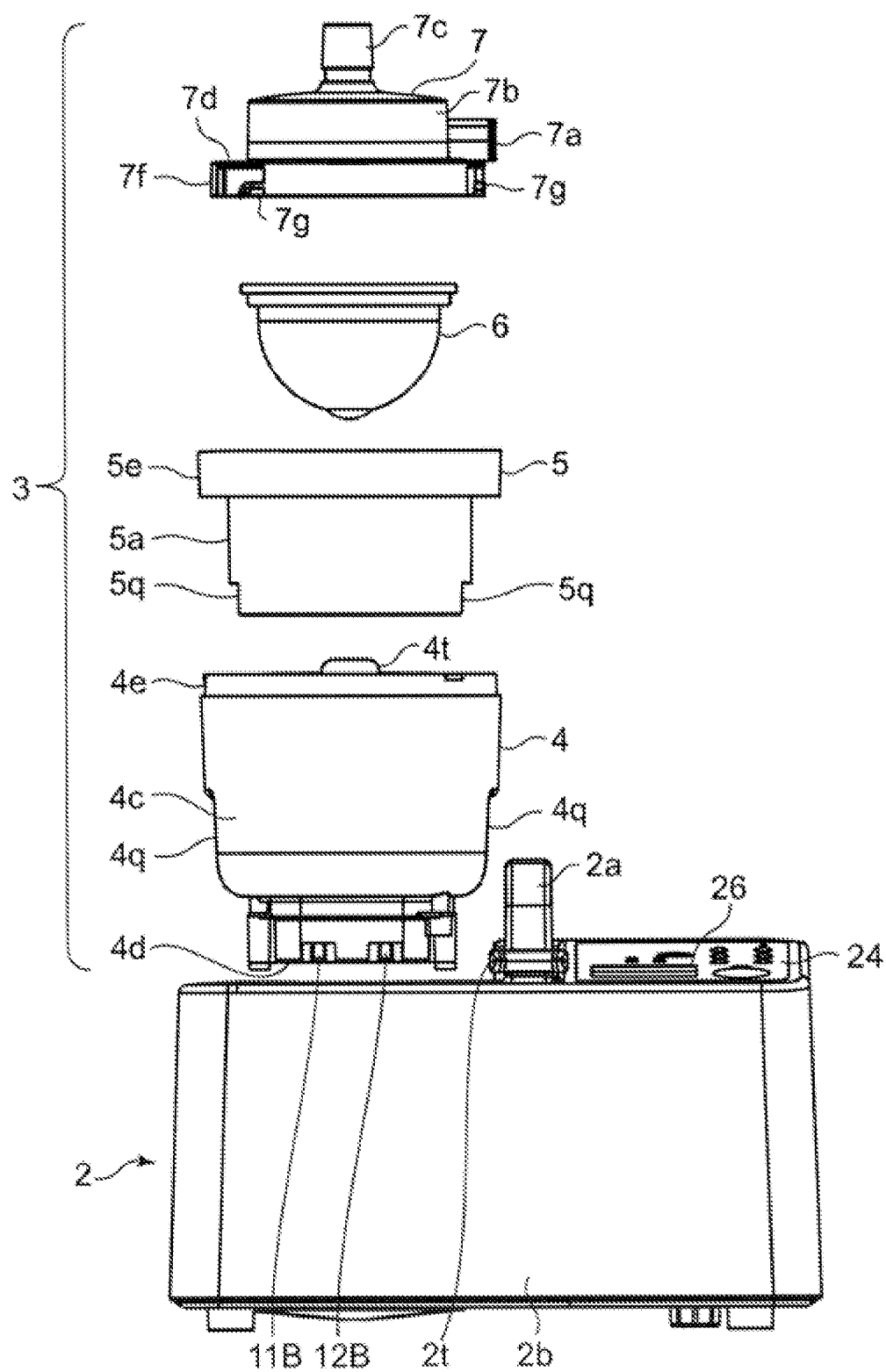
FIG. 2 is a diagram showing a view from the front of the ultrasonic nebulizer shown in FIG. 1.

FIG. 1 shows an exploded view from above and obliquely to the right of an ultrasonic nebulizer (indicated overall by reference numeral 1) of an embodiment of the invention. FIG. 2 shows a view from the front of the ultrasonic nebulizer shown in FIG. 1.

As can be understood from FIGS. 1 and 2, the ultrasonic nebulizer 1 generally includes a main body 2 and a tank unit 3 that is configured to be detachable with respect to the main body 2.

The tank unit 3 includes a working tank 4, a medicine tank support 5, a medicine tank 6, and a medicine tank cover 7.

The elements 4, 5, 6, and 7 of the tank unit 3 can be assembled by being overlaid in the stated order in a fit-together manner by the hand of a person without need for a tool, and can be disassembled in the inverse order.

The main body 2 includes a main portion 2b that forms a housing, and a carrying handle 2a that is provided on the upper surface of the main portion 2b and extends in the front-rear direction. An approximately cylindrical containing portion 2u for surrounding and containing the tank unit 3 is provided in the left half of the main portion 2b (leftward of the handle 2a). An opening 2w that is continuous with the containing portion 2u is provided on the rear surface side of the main portion 2b. The width (dimension in the left-right direction) of the opening 2w is set to be a dimension large enough that a person's fist can be inserted therein, for the sake of convenience in mounting the tank unit 3. A seating platform portion 2d (see FIGS. 3 and 4) on which the tank unit 3 is to be mounted is provided at the bottom of the containing portion 2u (below the main portion 2b). As shown in FIGS. 1 and 2, a C-shaped hose holder 2t for holding the leading end portion of an air suction hose 8 (see FIG. 9) attached to the medicine tank cover 7 is provided on the front portion of the handle 2a.

An operation switch portion 24, an LED (light-emitting diode) display unit 25, and an LCD (liquid crystal display element) display unit 26 are provided on the right half of the upper surface of the main body 2 (rightward of the handle 2a). The operation switch portion 24 includes a timer adjustment key switch 24A by which the user (a doctor, a nurse, or the like) inputs a continuous spray time, an air flow adjustment key switch 24B, which serves as a first operation portion and is for inputting an air flow setting value, an atomization amount adjustment switch 24C, which serves as a second operation portion and is for inputting an atomization amount setting value, and a spraying start/stop switch 24D for instructing the start or stopping of spraying. Note that the key switches 24A, 24B, and 24C each include an up key and a down key (indicated by the left and right pairs of circular marks in FIGS. 1 and 2) for increasing and reducing the input values. The LED display unit 25 and the LCD display unit 26 receive and display signals indicating the atomization amount, the air flow, the timer, the start of spraying, and states such as error from the later-described CPU 28 (see FIG. 9).

As shown in FIG. 1, a power switch 48 for the ultrasonic nebulizer 1 is provided on the right-side surface of the main body 2. Also, an air cover 2c that covers a later-described air fan is provided on the right rear portion of the main body 2.

Figure 5:
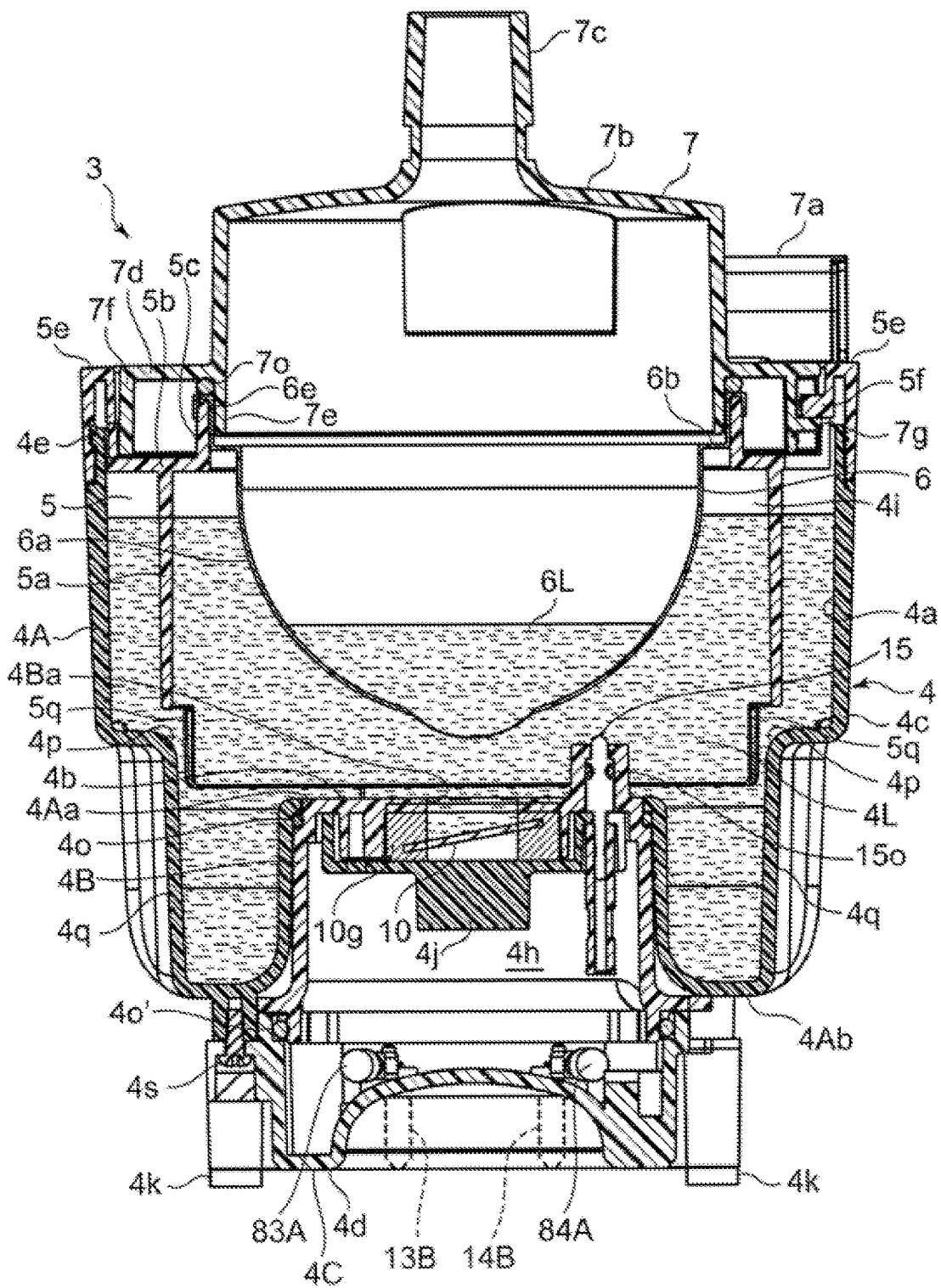
FIG. 5 is a longitudinal cross-sectional view (a cross-sectional view parallel to the surface of the page in FIG. 2) showing a configuration of the tank unit included in the ultrasonic nebulizer.
Figure 6:
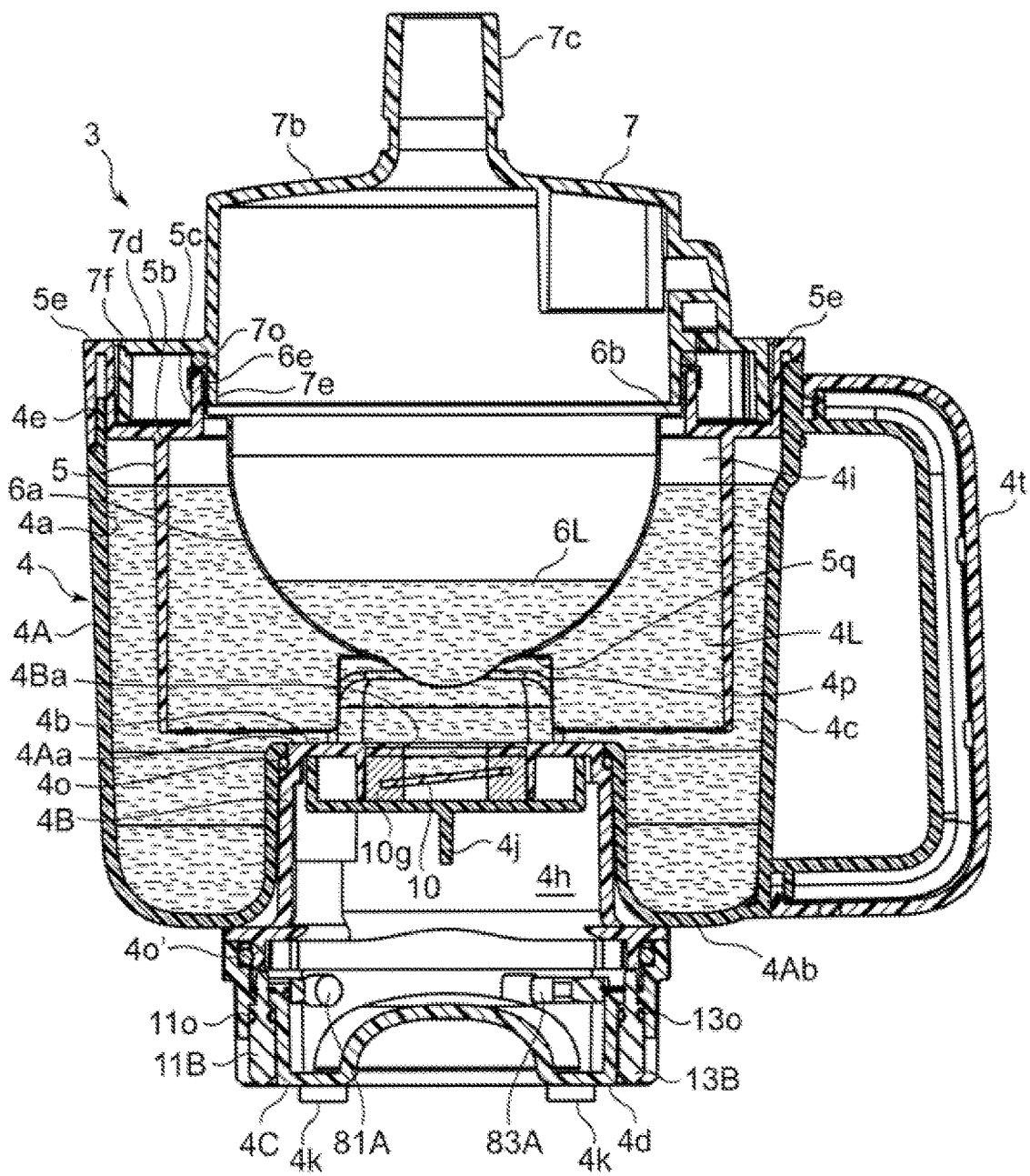
FIG. 6 is another longitudinal cross-sectional view (a cross-sectional view orthogonal to the surface of the page in FIG. 2) showing the configuration of the tank unit.

FIG. 5 shows a longitudinal cross section taken parallel to the page surface of FIG. 2, of the tank unit 3, which is in an assembled state. FIG. 6 shows a longitudinal cross section taken perpendicular to the page surface of FIG. 2, of the tank unit 3 in such a state.

As can be understood from FIGS. 5 and 6, the working tank 4 is open upward and includes: an approximately cylindrical inner circumferential wall 4a; an inner bottom surface that covers the lower portion of the inner circumferential wall 4a; an approximately cylindrical outer circumferential wall 4c that wraps around the inner circumferential wall 4a; an outer bottom surface 4d that covers the lower portion of the outer circumferential wall 4c; a top portion 4e that connects the upper edge of the inner circumferential wall 4a and the upper edge of the outer circumferential wall 4c; and a carrying handle 4t that is attached in an integrated manner to the outer circumferential wall 4c. A working liquid (in this example, water) 4L is contained in a tank inner space 4i, which is formed by the inner circumferential wall 4a and the inner bottom surface 4b, which constitute the inner surface of the working tank 4. A gap 4h is provided between the inner bottom surface 4b and the outer bottom surface 4d. Accordingly, the working tank 4 has a double-bottomed structure.

More specifically, the working tank 4 is constituted by a first member 4A composed of ABS (acrylonitrile butadiene styrene copolymer) resin, which forms the inner circumferential wall 4a and the outer circumferential wall 4c, a second member 4B composed of PPS (polyphenylene sulfide) resin, which forms the inner bottom surface 4b, and a third member 4C composed of PPS resin, which forms the outer bottom surface 4d. The first member 4A has an approximately cylindrical shape, has a lower portion 4Ab that is curved so as to protrude downward, and has an approximately circular opening 4Aa that is formed in a rising manner on the inner side. The second member 4B has an approximately cylindrical shape and the upper portion thereof fits watertightly into the opening 4Aa of the first member 4A via an O ring 4o. The upper portion of the second member 4B forms the inner bottom surface 4b of the working tank 4. An opening 4Ba is formed in the inner bottom surface 4b of the working tank 4 (second member 4B). The third member 4C has an approximately square tube-shaped outer shape and the upper portion thereof is fit watertightly around the lower portion of the second member 4B via an O ring 4o'. The lower portion of the third member 4C is closed and forms the outer bottom surface 4d of the working tank 4. The third member 4C is attached to the lower portion 4Ab of the first member 4A using multiple screws 4a (only one is shown in FIG. 5). As a result, the working tank 4 is integrally assembled in a state in which the second member 4B is interposed between the first member 4A and the third member 4C. Note that legs 4k of the working tank 4 are provided in a downwardly-projecting manner on the outer bottom surface 4d (third member 4C).

A plate-shaped ultrasonic vibrator 10 is incorporated in the gap 4h that forms the double-bottomed structure of the working tank 4. The vibrating surface of the ultrasonic vibrator 10 is arranged so as to face the tank inner space 4i from below the inner bottom surface 4b, through the opening 4Ba provided in the inner bottom surface 4b. More specifically, the ultrasonic vibrator 10 is held by being fit in a frame-shaped rubber holder 10g. The rubber holder 10g is pressed onto the periphery of the opening 4Ba of the inner bottom surface 4b from below by a pressing member 4j that is attached by a screw (not shown) to the inner bottom surface 4b. Accordingly, together with the holder 10g, the ultrasonic vibrator 10 is incorporated in a state in which the working liquid 4L does not leak from the tank inner space 4i through the opening 4Ba.

Also, a liquid level sensor 15 for detecting the liquid surface of the working liquid 4L is arranged at a predetermined height level of the tank inner space 4i. The liquid level sensor 15 generates a voltage signal that indicates whether or not the liquid level of the working liquid 4L in the working tank 4 exceeds the height level (necessary level). The liquid level sensor 15 is attached watertightly with an O ring 15o, penetrating through the inner bottom surface 4b.

Figure 9:
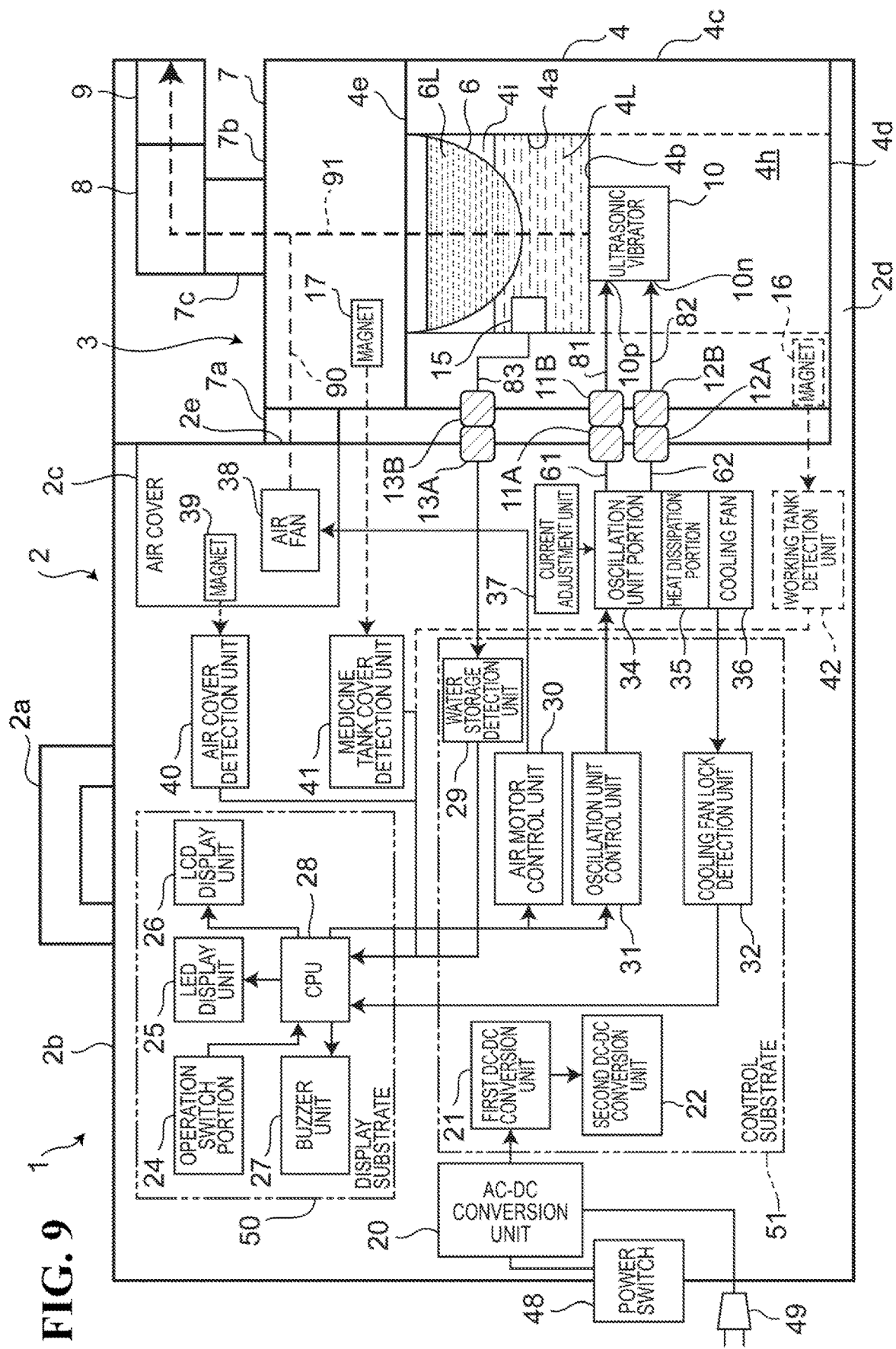
FIG. 9 is a diagram showing a schematic block configuration of the ultrasonic nebulizer.

In this example, first, second, third, and fourth tank-side contact electrodes 11B, 12B, 13B, and 14B are provided on the bottom portion (third member 4C) of the working tank 4 so as to penetrate through the outer wall (FIGS. 1 and 2 show the first and second tank-side contact electrodes 11B and 12B on the front surface side of the working tank 4, FIG. 5 shows the third and fourth tank-side contact electrodes 13B and 14B on the rear surface side of the working tank 4, and FIG. 6 shows the first and third tank-side contact electrodes 11B and 13B). The tank-side contact electrodes 11B, 12B, 13B, and 14B are attached watertightly to the outer wall with O rings (FIG. 6 shows O rings 11o and 13o that correspond to the first and third tank-side contact electrodes 11B and 13B). As shown in FIG. 9, the first and second tank-side contact electrodes 11B and 12B are connected to first and second electrodes 10p and 10n of the ultrasonic vibrator 10 by wires 81 and 82, respectively. Also, the third tank-side contact electrode 13B is connected to the liquid level sensor 15 by a wire 83. Note that metal members 81A and 83A in FIGS. 5 and 6 form portions of the wires 81 and 83. A metal member 84A is connected to a fourth tank-side contact electrode (dummy tank-side contact electrode) 14B.

Note that as shown in FIGS. 1 and 2 as well as FIGS. 5 and 6, with the working tank 4, specific locations (a left and right pair of locations in a view from the front) are curved toward the tank interior with respect to the circumferential direction of the first member 4A. Accordingly, a left and right pair of recesses 4q and 4q are formed in the outer circumferential wall 4c. Also, a left and right pair of protrusions 4p and 4p are formed in the inner circumferential wall 4a. The recesses 4q and 4q are used to guide the tank unit 3 (working tank 4) when the tank unit 3 (working tank 4) is mounted on the main body 2 (main portion 2b). The protrusions 4p and 4p are used to fix the orientation (direction) of the medicine tank support 5 with respect to the working tank 4.

As shown in FIGS. 1 and 2 as well as FIGS. 5 and 6, the medicine tank support 5 includes: a cylindrical portion 5a that is contained in the tank inner space 4i of the working tank 4, a flat support portion 5b that is provided along the upper end of the cylindrical portion 5a, an engagement portion 5e that is provided along the outer edge of the support portion 5b and opens downward with a C-shaped cross-section, and a projection portion 5c that is provided along the inner edge of the support portion 5b and projects upward. Cut-outs 5q and 5q that open downward in C shapes are formed at specific locations (a left and right pair of locations in a view from the front) with respect to the circumferential direction of the cylindrical portion 5a. As shown in FIGS. 5 and 6, the medicine tank support 5 is arranged overlaid on the working tank 4 from above due to the engagement portion 5e fitting into the top portion 4e of the working tank 4. At this time, the orientation (direction) of the medicine tank support 5 is fixed with respect to the working tank 4 by matching the cut-outs 5q with the projections 4p of the working tank 4. Conversely, if the medicine tank support 5 is pulled upward off of the working tank 4, the medicine tank support 5 is removed from the working tank 4. Note that in the medicine tank support 5, a projection 5f for locking the medicine tank cover 7 is provided at a specific location with respect to the circumferential direction on the inner side of the engaging portions 5e.

The medicine tank 6 includes a main portion 6a that is formed so as to protrude downward in an approximate hemispherical shape, a flat step portion 6b that is provided along the upper end of the main portion 6a, and an engagement portion 6e that is provided along the outer edge of the step portion 6b and opens downward with a C-shaped cross-section. Due to the engagement portion 6e fitting onto the projection portion 5c of the medicine tank support 5, the medicine tank 6 is arranged overlaid on the medicine tank support 5 from above. Conversely, if the medicine tank 6 is pulled upward off of the medicine tank support 5, the medicine tank 6 is removed from the medicine tank support 5. A medicinal liquid 6L that is to be atomized is contained in the medicine tank 6. Examples of the medicinal liquid 6L include a saline solution or a liquid mixture of a saline solution and Bisolvon. When the tank unit 3 is assembled, the bottom portion of the medicine tank 6 is dipped in the working liquid 4L in the working tank 4.

Figure 7:
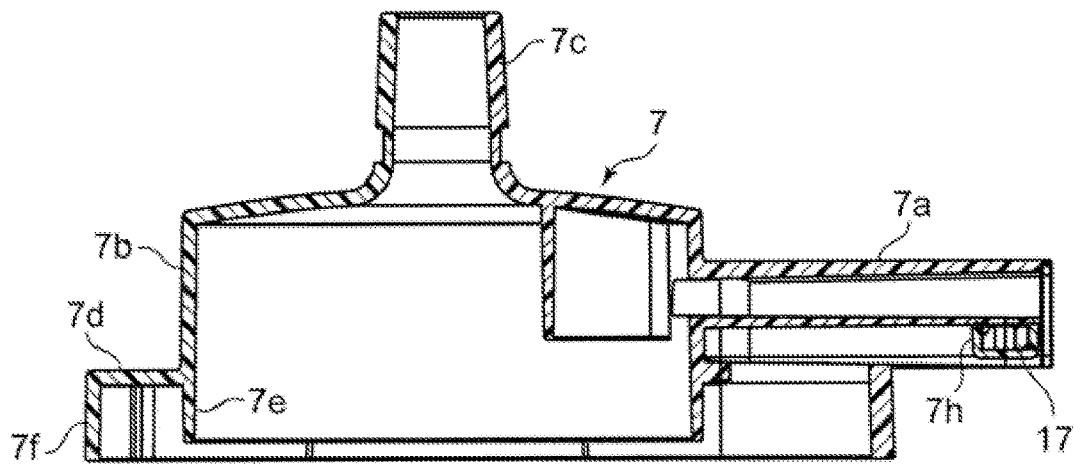
FIG. 7 is a cross-sectional view showing a configuration of a medicine tank cover included in the tank unit.

As shown in FIGS. 5 and 6, as well as in FIG. 7, which shows only the medicine tank cover 7, the medicine tank cover 7 includes: a simple cylindrical cover portion 7b with an upper portion that is closed so as to cover the upper portion of the medicine tank 6; an air duct 7a that is in communication with the cover portion 7b and extends laterally; and an emission port 7c that is in communication with the cover portion 7b and extends upward. Also, a flat flange portion 7d is formed along the periphery of the cover portion 7b. Furthermore, a ring-shaped outer edge portion 7f that projects downward is formed along the outer edge of the flange portion 7d. As shown in FIG. 7, together with a magnet attachment case 7h, a magnet 17 that is to be used to detect whether or not the medicine tank cover 7 has been mounted correctly on the main body 2 is incorporated on the lower portion of the entrance to the air duct 7a.

As shown in FIGS. 1, 2, and 5, an engagement portion 7g that is to be locked on the engagement portion 5e of the medicine tank support 5 is formed at a specific location with respect to the circumferential direction of the outer edge portion 7f on the medicine tank cover 7. As shown in FIGS. 5 and 6, the medicine tank cover 7 is arranged overlaid on the medicine tank 6 from above in a state in which an O ring 7o is attached around a lower portion 7e of the cover 7b. More specifically, the engagement portion 6e of the medicine tank 6 is pressed from above by the medicine tank cover 7 via the O ring 7o. Along with this, the engagement portion 7g is locked by passing below the projection 5f of the medicine tank support 5 due to the medicine tank cover 7 being rotated (in this example, clockwise in a view from above) slightly about the center (in the perpendicular direction) of the cover portion 7b. Accordingly, the medicine tank cover 7 is attached to the medicine tank support 5 in a mode in which the engagement portion 6e of the medicine tank 6 is interposed between the medicine tank cover 7 and the projecting portion 5c of the medicine tank support 5 via the O ring 7o, and the air duct 7a of the medicine tank cover 7 is arranged in a predetermined orientation (direction) with respect to the working tank 4 (the handle 4t of the working tank 4). In this example, in a view directly facing the handle 4t of the working tank 4, the entrance of the air duct 7a of the medicine tank cover 7 is arranged so as to face leftward. Conversely, if the medicine tank cover 7 is rotated slightly counterclockwise about the center of the cover portion 7b and the medicine tank cover 7 is pulled upward, the medicine tank cover 7 is removed.

Figure 3:
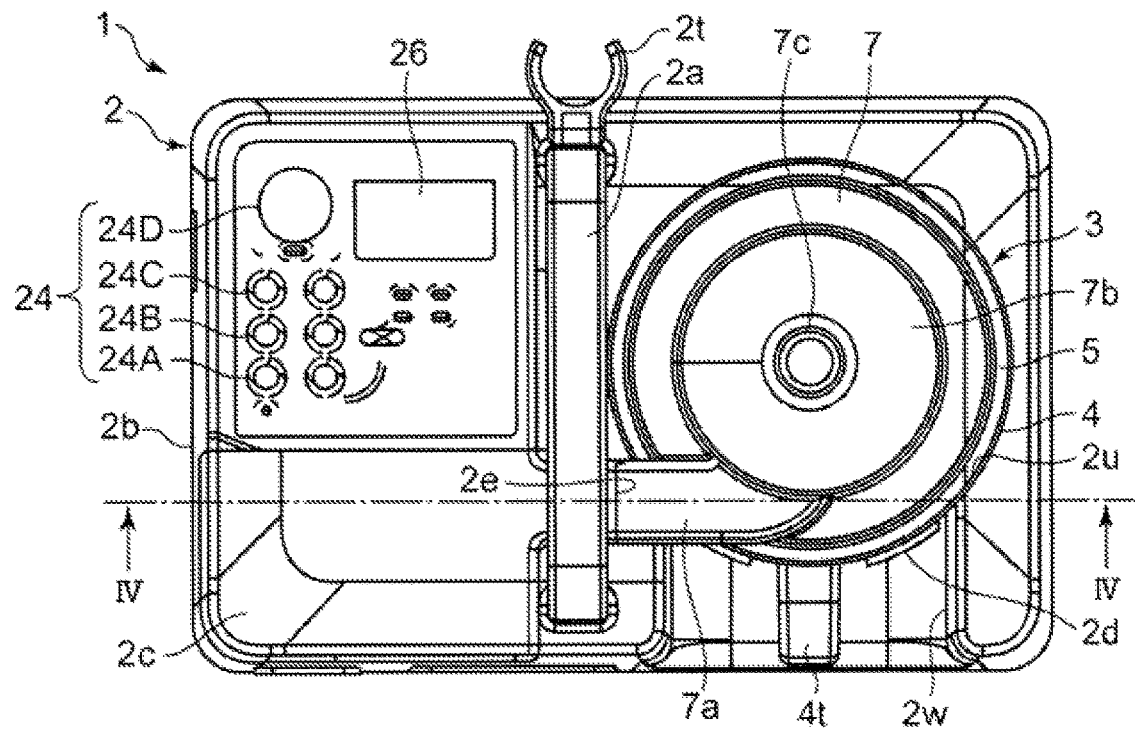
FIG. 3 is a diagram showing a view from above of the ultrasonic nebulizer in a tank unit mounted state.

FIG. 3 shows a view from above of a state (tank unit mounted state) in which the tank unit 3 is mounted on the main body 2 (the front surface of the main body 2 is drawn above, and the rear surface is drawn below). Also, FIG. 4 shows a cross-sectional view taken along line IV-IV in FIG. 3 and viewed in the direction of the arrows.

Figure 4:
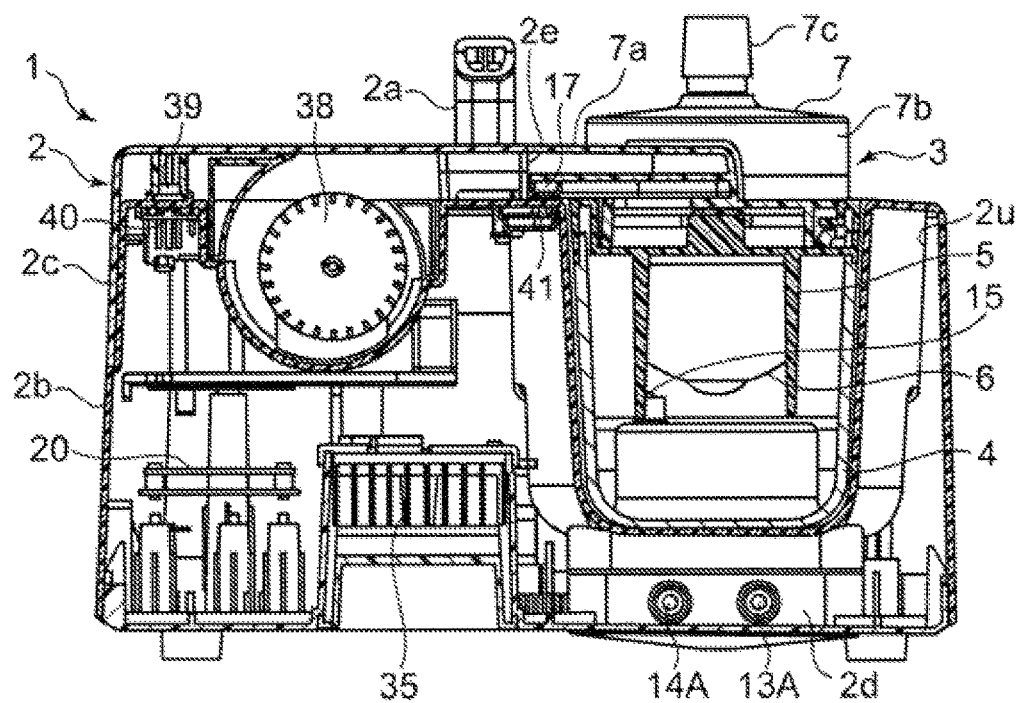
FIG. 4 is a diagram showing a cross-sectional view taken along line IV-IV in FIG. 3 and viewed in the direction of the arrows.

As shown in FIGS. 3 and 4, in the tank unit mounted state, the tank unit 3 is attached on the seating platform portion 2d on the bottom of the containing portion 2u of the main body 2. The tank unit 3 is attached in a mode in which the handle 4t of the working tank 4 faces rearward of the main body 2 and the outer side of the handle 4t approximately matches the rear surface of the main body 2. An arrangement is used in which the entrance of the air duct 7a of the medicine tank cover 7 extends above the main body 2 (main portion 2b). In the tank unit mounted state, the tank unit 3 is protected by being surrounded by the main body 2, and the tank unit 3 (particularly, the working tank 4) no longer detaches unexpectedly from the main body 2.

As shown in FIG. 4, an air fan (includes a motor that rotates the fan) 38 for blowing air to the medicine tank 6 is arranged on the upper portion of the main body 2 (main portion 2b). The air fan 38 is covered by an air cover 2c that can be detached from the main portion 2b. A vent 2e that communicates with the air duct 7a on the tank unit 3 side in the tank unit mounted state is provided in the air cover 2c. In the main portion 2b, a medicine tank cover detection unit 41 is provided at a location that corresponds to directly below the magnet 17 of the air duct 7a. The medicine tank cover detection unit 41 includes a hole IC (integrated circuit including a magnetic sensor) and uses the magnetic force of the magnet 17 incorporated in the medicine tank cover 7 to detect whether or not the medicine tank cover 7 has been correctly mounted on the main portion 2b (whether or not the air duct 7a matches the vent 2e).

Also, a magnet 39 that is used to detect whether or not the air cover 2c has been mounted on the main portion 2b is attached to the inner side of the air cover 2c. In the main portion 2b, the air cover detection unit 40 is provided at a location that corresponds to directly below the magnet 39 of the air cover 2c. The air cover detection unit 40 includes a hole IC and uses the magnetic force of the magnet 39 attached to the air cover 2c to detect whether or not the air cover 2c has been mounted on the main portion 2b.

A later-described AC-DC conversion unit 20 and a heat dispersion portion 35 are arranged in the lower portion in the main portion 2b.

Figure 8:
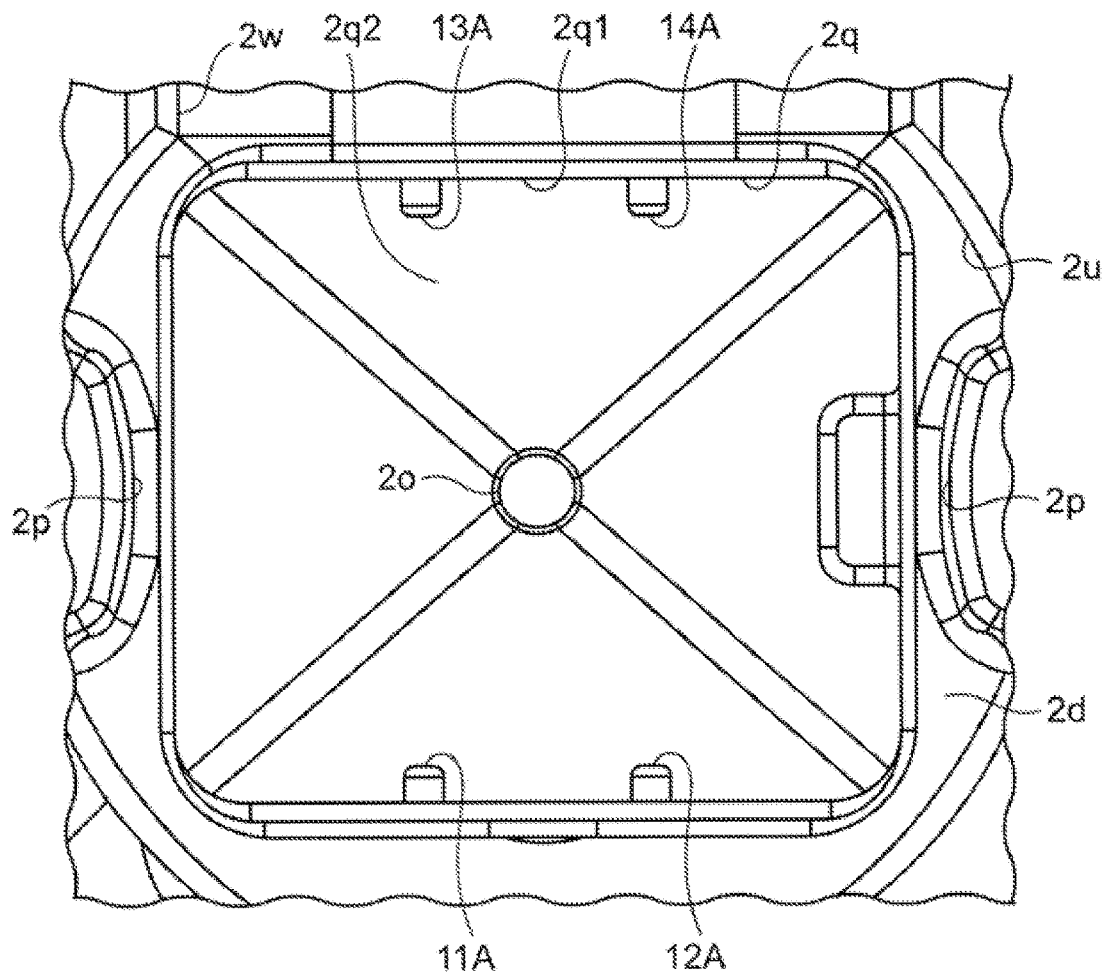
FIG. 8 is a diagram showing a view from above of a containing portion for containing the tank unit in the main body of the ultrasonic nebulizer.

FIG. 8 shows a view from above of the containing portion 2u for containing the tank unit 3 in the main body 2 (the front surface side of the main body 2 is drawn below and the rear surface side is drawn above). The protrusions 2p and 2p that are to be fit into the recesses 4q and 4q (see FIGS. 1 and 2) of the working tank 4 are formed at specific locations (a left and right pair of locations in a view from the front) with respect to the circumferential direction of the inner surface of the containing portion 2u. Approximately rectangular recesses 2q are formed on the seating platform portion 2d at the bottom of the containing portion 2u and the first, second, third, and fourth main body-side contact electrodes 11A, 12A, 13A, and 14A are provided so as to protrude from side walls 2q1 of the recesses 2q. The first, second, third, and fourth main body-side contact electrodes 11A, 12A, 13A, and 14A are biased in an orientation of protruding from the side walls 2q1 due to coil springs (not shown). Note that in the unlikely event that the working liquid 4L or the like is spilled, a bottom wall 2q2 of the recess 2q inclines so as to gradually become lower toward the center, and a liquid discharge port 2o is provided in the center of the bottom wall 2q2.

The working tank 4 (or the tank unit 3; the same follows hereinafter in this paragraph) is mounted on the seating platform portion 2d in the containing portion 2u of the main body 2 shown in FIG. 8 by being lowered from above in a standing orientation. At this time, the recesses 4q and 4q (see FIGS. 2 and 5) of the working tank 4 fit over the protrusions 2p and 2p on the inner surface of the containing portion 2u, and the working tank 4 is guided in a horizontal plane. Also, the orientation (direction) of the working tank 4 is set with respect to the main body 2 due to the approximately square tube-shaped bottom portion (third member 4C) of the working tank 4 being fit into the recess 2q of the seating platform portion 2b (note that the orientation of the working tank 4 with respect to the main body 2 is roughly set using the orientation of the handle 4t of the working tank 4). The first, second, third, and fourth main body-side contact electrodes 11A, 12A, 13A, and 14A come into contact with and connect to the first, second, third, and fourth tank-side contact electrodes 11B, 12B, 13B, and 14B of the working tank 4 respectively when the working tank 4 is lowered from above and seated. Conversely, the working tank 4 is removed from the main body 2 by being pulled upward from the seating platform portion 2d of the main body 2.

Thus, with the ultrasonic nebulizer 1, the working tank 4 is configured to be detachable with respect to the main body 2. Also, as stated above, the medicine tank 6 and the medicine tank cover 7 are configured to be detachable with respect to the working tank 4 via the medicine tank support 5. Accordingly, the user (a doctor, a nurse, or the like) can easily take out only the working tank 4 by first removing the tank unit 3 (includes the working tank 4, the medicine tank support 5, the medicine tank 6, and the medicine tank cover 7) from the main body 2 in the tank unit mounted state, and then removing the medicine tank cover 7, the medicine tank 6, and the medicine tank support 5 in the stated order from the working tank 4 of the tank unit 3. Alternatively, it is possible to easily take out only the working tank 4 by first removing the medicine tank 6 and the medicine tank cover 7 from the medicine tank support 5 in the tank unit mounted state, then removing the medicine tank support 5 from the working tank 4, and furthermore removing the working tank 4 from the main body 2. Accordingly, the working tank 4 can be easily cleaned and/or disinfected separately. Also, the medicine tank cover 7, the medicine tank 6, and the medicine tank support 5 can each be easily cleaned and/or disinfected with a disinfecting liquid separately.

FIG. 9 schematically shows a schematic block configuration of the ultrasonic nebulizer 1 (which is in the tank unit mounted state). Note that in FIG. 9, for the sake of simplicity, the medicine tank support 5, the fourth main body-side contact electrode 14A, and the fourth tank-side contact electrode 14B are not shown.

The main body 2 (main portion 2b) is provided with the above-described power switch 48, an AC (alternating current) plug 49, the AC-DC conversion unit 20, a display substrate 50, a control substrate 51, an oscillation unit portion 34, a heat dissipation portion 35 and cooling fan 36 that are arranged along the oscillation unit portion 34, a current adjustment unit 37, the air cover detection unit 40, and the medicine tank cover detection unit 41. In addition to the above-described operation switch portion 24, LED (light-emitting diode) display unit 25, and LCD (liquid crystal display element) display unit 26, the display substrate 50 is provided with a buzzer portion 27 and a CPU 28 that controls the overall operation of the ultrasonic nebulizer 1. The control substrate 51 is provided with a first DC-DC conversion unit 21, a second DC-DC conversion unit 22, a liquid shortage detection unit 29, an air-blowing motor control unit 30, an oscillation unit control unit 31, and a cooling fan lock detection unit 32.

The AC plug 49 is connected to a commercially-available AC power source (in this example, AC 100V). The power switch 48 is used to switch on and off the overall power of the ultrasonic nebulizer 1.

The AC-DC conversion unit 20 converts the AC 100V from the commercial AC power source into DC 48V. The DC 48V is used as a power source for causing the oscillation unit portion 34 and the ultrasonic vibrator 10 to operate.

The first DC-DC conversion unit 21 steps down the DC 48V to DC 12V. The DC 12V is used as a power source for causing the air cover detection unit 40, the air fan 38, and the cooling fan 36 to operate.

The second DC-DC conversion unit 22 steps down the DC 12V to DC 5V. The DC 5V is used mainly as system power to cause elements 24 to 28 on the display substrate 50 to operate.

As described above, the operation switch portion 24 is provided in order for a user (a doctor, a nurse, or the like) to perform switch input of an atomization amount, air flow, a timer, the start of spraying, and the like. The operation switch portion 24 transmits the switch input to the CPU 28.

Also, the LED display unit 25 and the LCD display unit 26 receive and display signals indicating the atomization amount, the air flow, the timer, the start of spraying, and states such as error from the CPU 28.

The buzzer portion 27 receives a signal indicating the end of a timer or a state such as error from the CPU 28 and performs notification using sound.

The liquid shortage detection unit 29 receives the voltage signal output from the liquid level sensor 15 in the tank unit mounted state and transmits a detection signal indicating whether or not the working liquid 4L in the working tank 4 has been filled to a necessary level in the CPU 28.

The air-blowing motor control unit 30 receives a PWM (pulse width modulation) signal for controlling the rotation rate of the air fan 38 from the CPU 28 and drives the air fan 38 according to the PWM signal.

In this example, the air fan 38 includes a sirocco fan, and a motor that rotates the sirocco fan at a rotation rate that corresponds to the PWM signal from the air-blowing motor control unit 30. The air fan 38 that is driven performs air-blowing 90 through the vent 2e to the tank unit 3 side.

The oscillation unit control unit 31 receives a PWM signal for controlling the atomization amount performed by the ultrasonic element 10 from the CPU 28 and transmits it to the oscillation unit portion 34.

In this example, the oscillation unit portion 34 includes a Colpitts oscillation circuit, receives a PWM signal for driving the ultrasonic vibrator 10 from the oscillation unit control unit 31, generates an oscillation waveform (AC oscillation potential) based on the PWM signal, and outputs the oscillation waveform to the ultrasonic vibrator 10.

In this example, the heat dissipation portion 35 is composed of a metal plate (copper plate, etc.) that has fins. The heat dissipation portion 35 emits heat transmitted from the oscillation unit portion 34 to the outside of the main body 2 using wind from the cooling fan 36.

The current adjustment portion 37 adjusts the current that the oscillation unit portion 34 allows to flow to the ultrasonic vibrator 10.

The cooling fan lock detection unit 32 receives a voltage signal (this will be called a "cooling fan lock signal") that is generated when the cooling fan 36 stops (locks) and converts it to a voltage level that can be input to the CPU 28. The voltage-converted cooling fan lock signal is input to the CPU 28. If the cooling fan locks, the CPU 28 performs control for displaying an error stating that the cooling fan 36 has stopped on the LED display unit 25 and the LCD display unit 26 and stopping the spraying operation.

As stated above, the air cover detection unit 40 uses the magnetic force of the magnet 39 attached to the air cover 2c to detect whether or not the air cover 2c has been mounted on the main portion 2b. A detection result indicating whether or not the air cover 2c has been mounted is input to the CPU 28. If the air cover 2c has not been mounted, the CPU 28 performs control for displaying an error stating that the air cover 2c has not been mounted on the LED display unit 25 and the LCD display unit 26 and stopping the spraying operation.

Also, the medicine tank cover detection unit 41 uses the magnetic force of the magnet 17 incorporated in the medicine tank cover 7 to detect whether or not the medicine tank cover 7 has been correctly mounted with respect to the main portion 2b (whether or not the air duct 7a matches the vent 2e). A detection result indicating whether or not the medicine tank cover 7 has been correctly mounted is input to the CPU 28. If the medicine tank cover 7 has not been correctly mounted, the CPU 28 performs control for displaying an error stating that the medicine tank cover 7 has not been correctly mounted on the LED display unit 25 and the LCD display unit 26 and stopping the spraying operation.

In the tank unit mounted state, as described above, the first and second main body-side contact electrodes 11A and 12A come into contact with and are connected to the first and second tank-side contact electrodes 11B and 12B, respectively. At the time of a spraying operation, the output from the oscillation unit portion 34 in the main body 2 is applied to the electrodes 10p and 10n of the ultrasonic vibrator 10 through the first and second main body-side contact electrodes 11A and 12A and the first and second tank-side contact electrodes 11B and 12B. Accordingly, the ultrasonic vibrator 10 in the working tank 4 is driven to generate ultrasonic vibration. The ultrasonic vibration is transmitted to the medicinal liquid 6L in the medicine tank 6 via the working liquid 4L, whereby the medicinal liquid 6L in the medicine tank 6 is atomized. The atomized medicinal liquid (aerosol) 91 is blown by the air-blowing 90 from the air fan 38, and in this example, is supplied to the patient through the suction hose 8 and the mouthpiece 9. Note that instead of the mouthpiece 9, it is possible to include an inhalation mask, a glass nasal olive for inhaling through the nostrils, or the like.

If the atomization operation is started simply based on an operation performed by a user while the tank unit 3 is not mounted on the main body 2, the output of the oscillation unit portion 34 will appear in the exposed main body-side contact electrodes 11A and 12A. For this reason, there is a risk that the user will receive an electric shock by touching the main body-side contact electrodes 11A and 12A. Also, with a method in which it is detected whether or not multiple elements (e.g., the working tank 4 and the medicine tank cover 7) comprising the tank unit 3 have been mounted, the configuration becomes complicated. Here, in this example, the tank unit 3 is included such that the working tank 4, the medicine tank support 5, the medicine tank 6, and the medicine tank cover 7 are arranged by being overlaid in the stated order. In other words, if the working tank 4, the medicine tank support 5, and the medicine tank 6 are not arranged, the medicine tank cover 7 cannot be arranged. Accordingly, if the medicine tank cover detection unit 41 detects that the medicine tank cover 7 has been correctly mounted (detects that the air duct 7a of the medicine tank cover 7 is adjacent to the main body 2 and matches the vent 2e), it is judged that all of the elements included in the tank unit 3 (the working tank 4, the medicine tank support 5, the medicine tank 6, and the medicine tank cover 7) have been mounted on the main body 2. In this case, the user cannot touch the main body-side contact electrodes 11A and 12A due to being blocked by the tank unit 3, and therefore even if the output of the oscillation unit portion 34 appears in the main body-side contact electrodes 11A and 12A, there is no risk that the user will receive an electric shock. On the other hand, if the medicine tank cover detection unit 41 detects that the medicine tank cover 7 has not been correctly mounted, there is a possibility that at least the medicine tank cover 7 among the constituent elements of the tank unit 3 has not been mounted on the main body 2. If the medicine tank cover 7 has not been mounted, there is a possibility that another constituent element of the tank unit 3 (the working tank 4, the medicine tank support 5, and the medicine tank 6) has not been mounted on the main body 2 as well. Accordingly, it is preferable to prohibit the output of the oscillation unit portion 34 from appearing in the main body-side contact electrodes 11A and 12A. In the case of doing so, even if the user touches the main body-side contact electrodes 11A and 12A, it is possible to eliminate the risk of electric shock.

Figure 10:
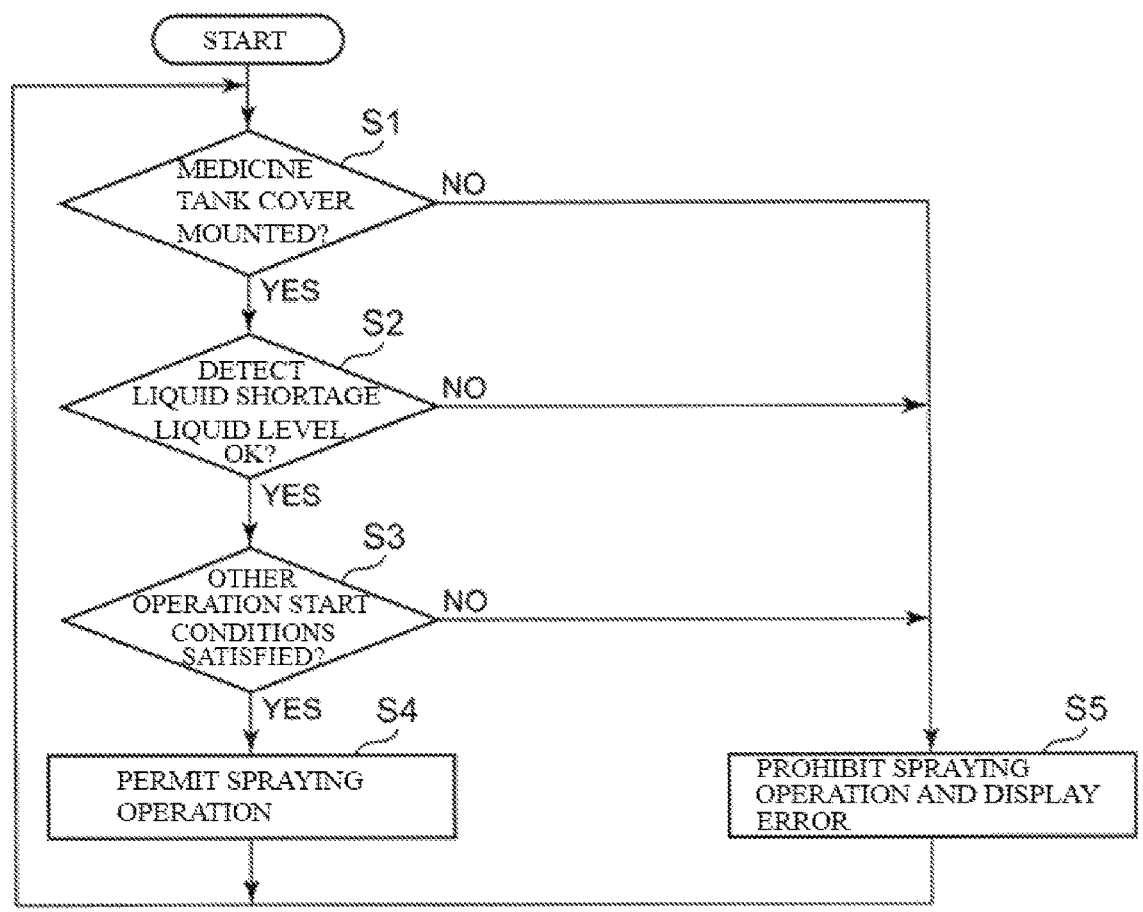
FIG. 10 is a diagram showing a flow of control performed by a CPU (central processing unit) provided in the main body.

FIG. 10 shows a control flow that was created according to the ideas described above, and according to which the CPU 28 acts as a control unit to judge whether or not the spraying operation (in which the atomization operation and the air-blowing operation are performed at the same time) is to be permitted.

i) When the power switch 48 of the main body 2 is switched on, as shown in step S1 in FIG. 10, based on the detection results of the medicine tank cover detection unit 41, the CPU 28 judges whether or not the medicine tank cover 7 has been correctly mounted on the main body 2 (whether or not the air duct 7a matches the vent 2e). Here, when the medicine tank cover 7 has not been correctly mounted (NO in step S1), an error stating that the medicine tank cover 7 has not been mounted is displayed on the LED display unit 25 and the LCD display unit 26 shown in FIG. 1, and a spraying operation prohibition flag indicating that the spraying operation is prohibited is set (step S5 in FIG. 10). On the other hand, when the medicine tank cover 7 has been correctly mounted (YES in step S1), it is judged that the tank unit 3 has been mounted on the main body 2, and the processing proceeds to the next step S2.

ii) In step S2, based on the detection result of the liquid shortage detection unit 29, the CPU 28 judges whether or not the working liquid 4L in the working tank 4 has been filled to the necessary level. Here, when the working liquid 4L in the working tank 4 has not been filled to the necessary level (NO in step S2), an error indicating that the working liquid 4L in the working tank 4 is insufficient is displayed on the LED display unit 25 and the LCD display unit 26 shown in FIG. 1, and a spraying operation prohibition flag indicating that the spraying operation is to be prohibited is set (step S5 in FIG. 10). On the other hand, in step S2, when the working liquid 4L in the working tank 4 has been filled to the necessary level (YES in step S2), the processing proceeds to the next step S3.

iii) In step S3, the CPU 28 determines whether or not other operation start conditions have been satisfied. Examples of the other operation start conditions include the cooling fan 36 shown in FIG. 9 not being stopped (or locked) (detected by the cooling fan lock detection unit 32), or the air cover 2c being mounted (detected by the air cover detection unit 40). If the other operation start conditions have not been satisfied (NO in step S3), an error indicating the unsatisfied operation start conditions is displayed on the LED display unit 25 and the LCD display unit 26 shown in FIG. 1, and the spraying operation prohibition flag is set (step S11 in FIG. 10).

iv) On the other hand, if the other operation start conditions have been satisfied in step S3 of FIG. 10 (YES in step S3), the CPU 28 advances the processing to step S4, cancels the spraying operation prohibition flag, and sets a spraying operation permission flag indicating that the spraying operation is permitted. Accordingly, it is possible to permit the spraying operation only if all of the operation start conditions have been satisfied.

As long as the power switch 48 of the main body 2 is on, the CPU 28 periodically repeats the processing of steps S1 to S5. Then, when the spraying start switch 24D of the operation switch portion 24 is pressed while the spraying operation permission flag is set, the CPU 28 performs control for starting the spraying operation. On the other hand, even if the spraying start switch 24D of the operation switch portion 24 is pressed while the spraying operation prohibition flag is set, the spraying operation will not be started.

Thus, according to the ultrasonic nebulizer 1, if the medicine tank cover 7 has first been correctly mounted on the main body 2, the CPU 28 judges that the tank unit 3 has been mounted on the main body 2 (step S1 in FIG. 10), and then the CPU 28 judges whether or not the working liquid 4L in the working tank 4 has been filled to the necessary level, which is a prerequisite for mounting the tank unit 3 (step S2 in FIG. 10). In other words, by judging whether or not the medicine tank cover 7 has been correctly mounted on the main body 2, it is judged whether or not the tank unit 3 has been mounted on the main body 2. Also, the spraying operation is permitted or prohibited based on an operation start condition, which is that the medicine tank cover 7 has been correctly mounted on the main body 2. Accordingly, it is possible to eliminate the risk of electric shock without detecting whether or not the working tank 4, which is included in the tank unit 3, has been mounted. For example, in order to detect whether or not the working tank 4 has been mounted, there is no need to provide the magnet 16 in the working tank 4 or to provide the working tank detection unit (includes the hole IC) 42 for detecting the magnetic force of the magnet 16 in the main body 2, as indicated by the broken lines in FIG. 9 for example. Accordingly, it is possible to eliminate the risk of electric shock with a simple configuration.

Also, the method for detecting the mounting of the medicine tank cover 7 is a method in which the magnet 17 is provided in the air duct 7a of the medicine tank cover 7 and detection is performed using the medicine tank cover detection unit 41, which includes a hole IC, and therefore it is possible to use a simple and inexpensive configuration.

With the above-described flow of FIG. 10, in order for the CPU 28 to judge whether or not to permit the spraying operation, it is sequentially judged whether or not the medicine tank cover 7 has been mounted (step S1), whether or not the liquid level of the working liquid 4L is sufficient (step S2), and whether or not the other operation start conditions have been satisfied (step S3). However, the sequence of judging is not limited thereto, and for example, judging may be performed in parallel (parallel processing), for example.

Figure 11:
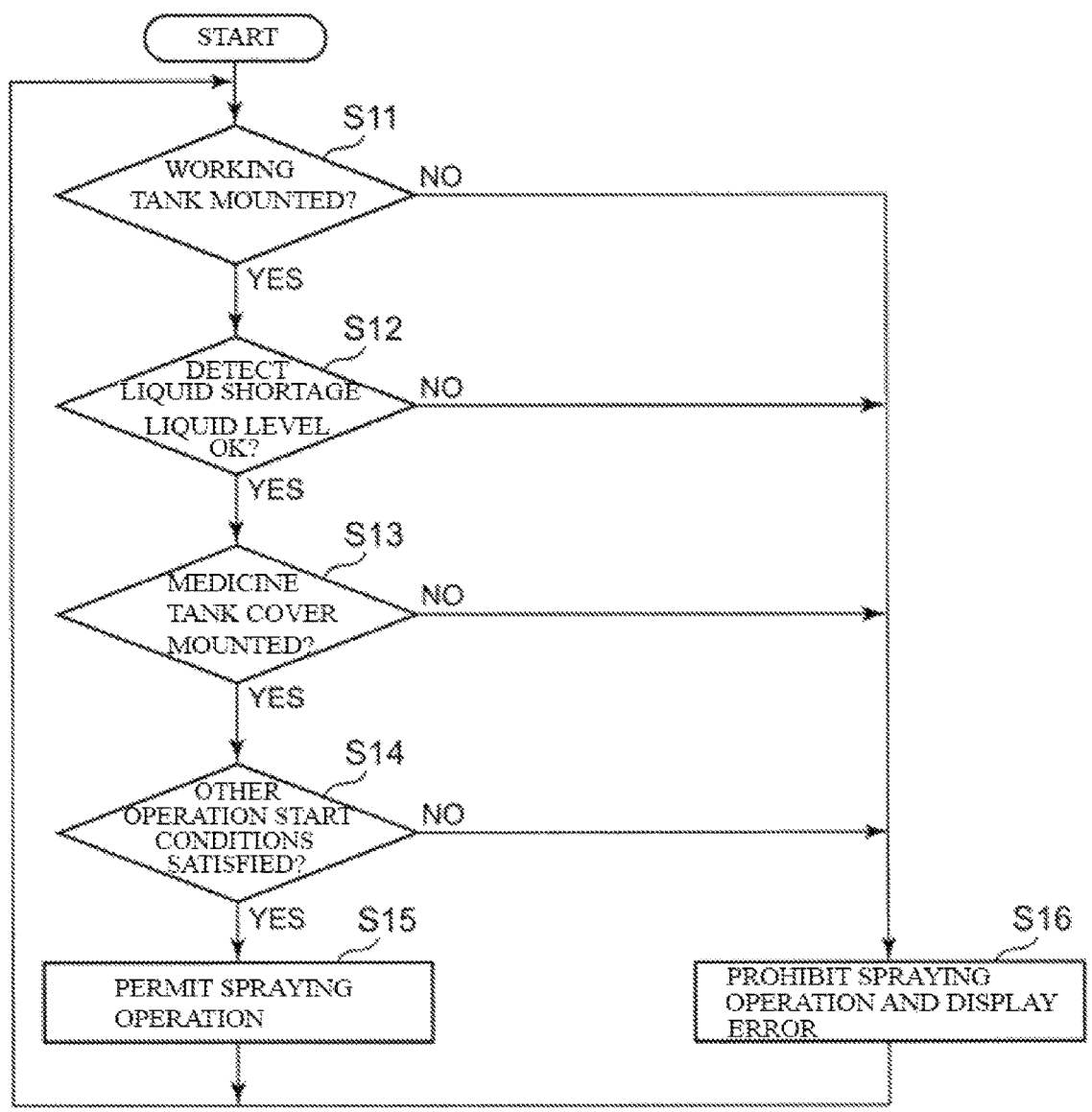
FIG. 11 is a diagram showing a control flow of a comparative example of the flow shown in FIG. 10.

FIG. 11 shows a control flow of a comparative example of FIG. 10. This control flow envisions that a working tank detection unit for detecting whether or not the working tank 4 is mounted on the main body 2 is provided (e.g., that a magnet 16 is provided in the working tank 4 and the working tank detection unit (includes a hole IC) 42 that detects the magnetic force of the magnet is provided in the main body 2, as indicated by the broken lines shown in FIG. 9).

i) When the power switch of the main body 2 is turned on, as shown in step S11 of FIG. 11, the CPU 28 determines whether or not the working tank 4 has been mounted on the main body 2 based on the detection results of the working tank detection unit 42. Here, when the working tank 4 has not been mounted (NO in step S11), an error indicating that the working tank 4 has not been mounted is displayed on the LED display unit 25 and the LCD display unit 26 shown in FIG. 1, and a spraying operation prohibition flag indicating that the spraying operation is prohibited is set (step S16 in FIG. 11). On the other hand, when the working tank 4 has been mounted on the main body 2 (YES in step S11), the processing advances to the next step S12.

ii) In step S12, the CPU 28 judges whether or not the working liquid 4L in the working tank 4 has been filled to the necessary level, based on the detection result of the liquid shortage detection unit 29. Here, when the working liquid 4L in the working tank 4 has not been filled to the necessary level (NO in step S12), an error indicating that the working liquid 4L in the working tank 4 is insufficient is displayed on the LED display unit 25 and the LCD display unit 26 shown in FIG. 1, and a spraying operation prohibition flag indicating that the spraying operation is prohibited is set (step S16 in FIG. 11). On the other hand, in step S12, when the working liquid 4L in the working tank 4 has been filled to the necessary level (YES in step S12), the processing advances to the next step S13.

iii) In step S13, the CPU 28 judges whether or not the medicine tank cover 7 has been correctly mounted on the main body 2 (main portion 2b) (whether or not the air duct 7a matches the vent 2e), based on the detection result of the medicine tank cover detection unit 41. Here, when the medicine tank cover has not been correctly mounted on the main body 2 (main portion 2b) (NO in step S13), an error indicating that the medicine tank cover 7 has not been correctly mounted is displayed on the LED display unit 25 and the LCD display unit 26 shown in FIG. 1, and a spraying operation prohibition flag indicating that the spraying operation is prohibited is set (step S16 in FIG. 11). On the other hand, in step S13, when the medicine tank cover has been mounted correctly (YES in step S13), the processing advances to the next step S14.

iv) Next, in step S14 in FIG. 11, the CPU 28 judges whether or not the other operation start conditions have been satisfied. Examples of the other operation start conditions include the cooling fan 36 shown in FIG. 9 not being stopped (or locked) (detected by the cooling fan lock detection unit 32), or the air cover 2c being mounted (detected by the air cover detection unit 40). If the other operation start conditions have not been satisfied (NO in step S14), an error indicating the unsatisfied operation start conditions is displayed on the LED display unit 25 and the LCD display unit 26 shown in FIG. 1, and the spraying operation prohibition flag is set (step S16 in FIG. 11).

v) On the other hand, if the other operation start conditions have been satisfied in step S14 in FIG. 11 (YES in step S14), the CPU 28 advances to step S15, the spraying operation prohibition flag is cancelled, and a spraying operation permission flag indicating that the spraying operation is permitted is set. Accordingly, it is possible to permit the spraying operation only if all of the operation start conditions have been satisfied.

As long as the power switch 48 of the main body 2 is on, the CPU 28 periodically repeats the processing of steps S11 to S16. Then, when the spraying start switch 24D of the operation switch portion 24 is pressed while the spraying operation permission flag is set, the CPU 28 performs control for starting the spraying operation. On the other hand, even if the spraying start switch 24D of the operation switch portion 24 is pressed while the spraying operation prohibition flag is set, the spraying operation will not be started.

Accordingly, it is possible to eliminate the risk of electric shock with the flow shown in FIG. 11. Note that compared to the control flow in FIG. 10, the step count has increased by one step, which is step 11 for first detecting whether or not the working tank 4 has been mounted on the main body 2. Note that the sequence of judging in FIG. 11 is not limited thereto, and judging may be performed in parallel (parallel processing) for example, similar to the description given regarding the flow shown in FIG. 10.

The above-described embodiment is merely an example and can be modified in various ways without departing from the scope of the invention. The various characteristics of the above-described embodiment can be realized independently, but it is also possible to combine the characteristics.

REFERENCE SIGNS LIST

1 Ultrasonic nebulizer
2 Main body
2u Containing portion
3 Tank unit
4 Working tank
5 Medicine tank support
6 Medicine tank
7 Medicine tank cover
7a Air duct
10 Ultrasonic vibrator

The invention claimed is:

1. An ultrasonic nebulizer comprising a tank unit configured to be detachable with respect to a main body,
wherein the tank unit includes:
a working tank in which an ultrasonic vibrator is incorporated and in which a working liquid is contained facing the ultrasonic vibrator;
a medicine tank that stores a medicinal liquid, at least a bottom portion thereof being dipped in the working liquid; and
a medicine tank cover that covers an upper portion of the medicine tank and has an air duct that is adjacent to the main body when the tank unit is mounted on the main body, the air duct being configured to take in blown air from the main body side,
the working tank, the medicine tank, and the medicine tank cover are configured to be arranged overlaid in the stated order,
the tank unit further includes a tank-side contact electrode that is connected to an electrode of the ultrasonic vibrator,
the main body includes:
a side wall configured to receive the tank unit;
an oscillation circuit configured to drive the ultrasonic vibrator; and
a main body-side contact electrode that is protruding from the side wall and that is configured to emit an output of the oscillation circuit,
when the tank unit is mounted on the main body, the main body-side contact electrode and the tank-side contact electrode are configured to apply the output of the oscillation circuit to the ultrasonic vibrator, and
the main body further includes:
an air fan configured to blow air into the medicine tank through the air duct of the medicine tank cover; and
a medicine tank cover detection unit configured to detect whether or not the air duct of the medicine tank cover is adjacent to the main body, so as to detect whether or not the tank unit is mounted on the main body.

2. The ultrasonic nebulizer according to claim 1, comprising
   a control unit configured to perform control for permitting or prohibiting an atomization operation based on an operation start condition, which is that the medicine cover detection unit has detected that the air duct is adjacent to the main body.
3. The ultrasonic nebulizer according to claim 2, wherein
   a magnet is incorporated in the air duct, and
   the medicine tank cover detection unit is configured to use the magnetic force of the magnet to detect whether or not the air duct is adjacent to the main body.
4. The ultrasonic nebulizer according to claim 1, wherein
   a magnet is incorporated in the air duct, and
   the medicine tank cover detection unit is configured to use the magnetic force of the magnet to detect whether or not the air duct is adjacent to the main body.

* * * * *